US005435934A

United States Patent [19]

Jon et al.

[11] Patent Number: 5,435,934

[45] Date of Patent: Jul. 25, 1995

[54] CONVERSION OF WATER-INSOLUBLE SOAP SCUM INTO A STABILIZED WATER-SOLUBLE DISPERSION

[75] Inventors: Domingo I. Jon, New York, N.Y.; John C. Hornby, Washington Township, N.J.

[73] Assignee: ISP Investments Inc., Wilmington, Del.

[21] Appl. No.: 235,813

[22] Filed: Apr. 28, 1994

Related U.S. Application Data

[63] Continuation-in-part of Ser. No. 937,036, Aug. 31, 1992, abandoned.

[51] Int. Cl.$^6$ .......................... C11D 9/04; C11D 9/30; C07C 209/00

[52] U.S. Cl. .......................... 252/117; 252/DIG. 16; 252/173

[58] Field of Search ............... 252/117, DIG. 16, 173; 424/70

[56] References Cited

U.S. PATENT DOCUMENTS

| | | | |
|---|---|---|---|
| 3,988,318 | 10/1976 | Copes et al. | 252/106 |
| 4,265,778 | 5/1981 | Sonnestein | 252/117 |
| 4,834,970 | 5/1989 | Login et al. | 424/70 |
| 5,093,031 | 3/1992 | Login et al. | 252/357 |
| 5,198,209 | 3/1993 | Zhou et al. | 424/70 |
| 5,252,245 | 10/1993 | Garabedian, Jr. et al. | 252/153 |

*Primary Examiner*—Prince Willis, Jr.
*Assistant Examiner*—James M. Silbermann
*Attorney, Agent, or Firm*—Walter Katz; Marilyn J. Maue; Joshua J. Ward

[57] ABSTRACT

Water-insoluble soap scum is converted into a stabilized, water-soluble dispersion which does not adhere to a hard surface. The process comprising applying a formulation containing a N-alkyl substituted lactam to the soap scum.

4 Claims, No Drawings

CONVERSION OF WATER-INSOLUBLE SOAP SCUM INTO A STABILIZED WATER-SOLUBLE DISPERSION

CROSS-REFERENCE TO RELATED PATENT APPLICATION

This is a continuation-in-part of patent application Serial No. 07/937,036, filed Aug. 31, 1992, now abandoned.

BACKGROUND OF THE INVENTION

1. Field of the Invention

This invention relates to a process for converting water-insoluble soap scum into a stabilized, water-soluble dispersion by contacting the soap scum with a formulation containing an N-hydrocarbon-substituted lactam.

2. Description of the Prior Art

Login, in U.S. Pat. No. 5,093,031, describes an N-alkyl substituted lactam having improved surfactant and complexing properties, and several uses thereof. However, none of the examples or description therein relate to a process or soap formulations which can convert water-insoluble soap scum formed during use into a water-soluble dispersion which does not adhere to hard surfaces.

SUMMARY OF THE INVENTION

A method and soap formulation is described for transforming water-insoluble soap scum into a water-soluble dispersion which does not adhere to a solid surface, which comprises applying to the soap scum a formulation containing about 0.05–5% by weight of an N-alkyl substituted lactam having the formula

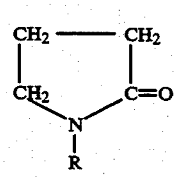

where R is a hydrophobic radical selected from linear and branched chain alkyl groups having from 5–27 carbon atoms.

BRIEF DESCRIPTION OF THE INVENTION

The formulations used herein includes 0.05–5% by weight of a distinctive group of N-hydrocarbon substituted lactams having unusual properties and defined by the formula

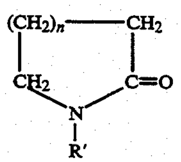

A.

wherein n is an integer having a value of from 1 to 3 and R′ is a hydrophobic radical selected from the group consisting of a linear, branched chain or cyclic alkyl radical containing from 5 to 27 carbon atoms; a naphthyl or alkyl substituted naphthyl radical containing from 10 to 26 carbon atoms and an alkylphenyl or phenylalkyl radical containing from 9 to 26 carbon atoms. Of the above lactam surfactants, the N-alkyl lactams are preferred and, of these, N-alkyl pyrrolidones containing 5 to 18 carbon atoms are most preferred.

While it is intended to include lactams substituted with cycloalkyl R′ groups, it is found that the hydrophobic affect of these cyclic groups is less than that of their linear analogs. Accordingly, where a N-cycloalkyl R′ group is intended, the R′ moiety contains at least 8 carbon atoms to provide hydrophobic-lipophobic balance.

It is also intended to include lactams wherein one of the hydrogen atoms bonded to a carbon atom member of the heterocyclic ring can be substituted with methyl or ethyl.

The cyclic hydrophilic moiety of the compounds herein defined is an important factor in maximizing their efficiency by concentrating the molecule, and thus the surfactant activity, at the interface and minimizing solubility of the molecule in liquid phases.

The above properties demonstrate the high efficiency and activity of the present nonionic surfactants. Such surfactant properties are unexpected since the compounds lack the polyalkoxy groups commonly associated with conventional nonionic surfactants. By way of comparison, N-dodecyl-2-pyrrolidone, exhibits a surfactant properties equivalent to a lauryl alcohol containing 5 moles of ethoxylate, i.e. $C_{12}H_{25}-(CH_2CH_2O)_5H$, a known commercial nonionic surfactant.

Not all of the present lactams possess good aqueous surfactant properties. For example, the R′ alkyl substituents of hexadecyl and above exhibit an imbalance such that the hydrophilic pyrrolidone or caprolactam moiety cannot counteract the dominating hydrophobic character of the alkyl group. However, these higher molecular weight compounds can provide surfactant properties in non-aqueous systems and are valuable wetting agents in applications involving solid substrates.

The structure of the present lactams provides a key to their unique properties. Specifically, the highly polar and hydrophilic pyrrolidone moiety exhibits several resonance forms, i.e.

B.

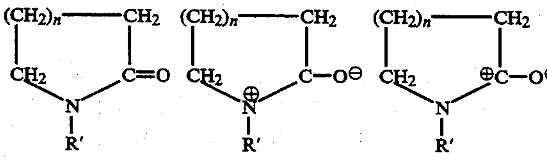

The existence of such multiple resonance states contributes to the high dipole moment of about 4 debye, possessed by these lactams. A high dipole moment is an important property, conferring the ability of these molecules to assume multiple resonance forms which promotes their tendency to complex or interact with many chemical groups. For example, the ability of these compounds to interact with anionic moieties, e.g. sulfate groups, is beneficial in enhancing foam and reducing skin irritability of various medicinal creams and lotions containing such or similar anionic groups.

The above lactam products having a molecular weight of from about 180 to about 450 are conveniently prepared by several known processes including the reaction between a lactone having the formula

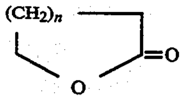

C.

wherein n is as defined above, and an amine having the formula $R'-NH_2$ wherein R' is as defined above. The amine reactant having the formula $R'-NH_2$ includes alkyl amines having from 7 to 20 carbon atoms; naphthyl or alkylnaphthyl amines having from 10 to 26 carbon atoms; alkylphenyl or phenylalkyl amines having from 9 to 26 carbon atoms; amines derived from natural products, such as coconut amines or tallow amines and distilled cuts or hydrogenated derivatives of such fatty amines. Also, mixtures of amine reactants can be used in the process for preparing the present compounds. Such mixtures can include cyclic, linear and branched chain amino species having an alkyl or other organic substituent of the same of different molecular weight. In the present process the amine and lactone reactants, combined in a mole ratio of from about 1:1 to about 1:5, are reacted under conditions of constant agitation, at a temperature between about 200° C. and about 350° C. under a pressure of from atmospheric to about 650 psig for a period of from about 1 to about 15 hours; preferably at 250° C. to 300° C. under an initial ambient pressure for a period of from 5 to 10 hours. The resulting lactam product is recovered and purified by distillation or by any other convenient recovery process.

The N-alkyl lactam products having 11 to 14 carbon atoms are clear, water white liquids, at room temperature; whereas those having 16 or more carbon atoms are solids. These lactams have a neutral or slightly basic pH, a surface tension between about 25 and about 35 dynes/cm as a 0.1% water solution and a viscosity of from about 6 to about 30 cps at 25° C. Generally, the $C_8$ to $C_{14}$ alkyl lactams display primarily surfactant properties; whereas the $C_{16}$ to $C_{22}$ alkyl species are primarily complexing agents; although some degree of surfactants and complexing capability exists in all of the present species.

Illustrative formulations for converting water-insoluble soap scum into a stabilized water-soluble dispersion according to the invention are the following:

| BAR SOAPS | |
|---|---|
| (A) | |
| Tallow/Coco Soap (90/10) | 67% by weight |
| Surfadone ® LP-100* | 1 |
| Igepal DM-970 | 20 |
| Igepon AC-78 | 12 |
| | 100% |
| (B) | |
| Tallow/CoCo Soap (90/10) | 18% by weight |
| Stearic Acid | 26 |
| Surfadone ® LP-100 | 2 |
| Igepon AC-78 | 40 |
| Igepal DM-970 | 14 |
| | 100% |
| (C) | |
| Sodium Lauryl Sulfate (30%) | 30% |
| Varox 185E | 2.5% |
| Glycerine | 0.5% |
| Glycol Monostearate | 1.3% |
| Surfadone LP-100 | 1.0% |
| Phosphoric Acid to pH 6.8, Dye and Perfume | Q.S. |
| Sodium Chloride | 1.7% |
| Water to | 100% |

-continued

| BAR SOAPS | |
|---|---|
| (D) | |
| Distilled Water | 57.2% |
| Gafquat 755N | 2.5% |
| Alipal CO-433 | 25.0% |
| Citric Acid, 20% solution | 0.3% |
| Surfadone ® LP-100 | 1.0% |
| Cocamidopropyl Betaine | 15.0% |
| Fragrance | Q.S. |
| Preservative | Q.S. |

*N-octylpyrrolidone

Commercial soap bars, such as IVORY® or DOVE®, in the presence of 150 ml of a solution of 300 mg/1 of hard water, ($Ca^{++}/mg^{++}=6:4$) produced a gel like precipitate, or soap scum, in discrete sizes, which upon stirring, broke down into smaller sizes, and which, upon wetting, agglomerated and precipitated onto hard surfaces.

In contrast, the presence of Surfadone®LP-100 (0.06%) in a solution of 300 mg/liter of hard water in the presence of soap (50 ml of Ivory soap foam) transformed the insoluble soap-scum into a stabilized water-soluble dispersion which did not adhere to glass surfaces.

When the foam of a soap solution was brought in contact with hard water (300 mg/liter of $Ca^{++}$:Mg (6:4 ratio)) an insoluble gel-like precipitate appeared due to the complexation of the positive divalent ions with the negatively charged carboxylate ions. However, with the addition of 0.06% Surfadone® LP-100 in hard water, a cloudy, stabilized water-soluble dispersion of the precipitate was obtained.

A solution of hard water containing 300 mg of calcium ions and magnesium ions at 6:4 ratio was used to compare the solubility of a commercial soap. 150 ml of the hard water solution was set aside and 0.06 Surfadone LP-100 was added to it.

EXAMPLES

1. Control

A soap solution of Ivory® soap was prepared at a concentration of 1 gram of soap per liter of solution. 150 ml of the soapy solution was transferred to a Waring® blender and stirred for 2 minutes. Afterwards, approximately 50 ml of the foam was transferred to a container with 100 ml of hard water (300 mg/1 of $Ca^{++}/mg^{++}$ (6:4)). Addition of the foam to the hard water solution created a gel-like film on the water surface which was a complex between the anionic soap and the positive divalent cation calcium and magnesium ions. The film later precipitated and did not disperse in water; instead, it remained on the glass surfaces of the container. Upon settling, the precipitate agglomerated and soap scum particles adhered stubbornly to the glass surfaces.

2. Invention

When the same amount of foam was added to a solution of hard water containing 0.06% of Surfadone® LP-100, a gel-like film was formed. Later the film remained on the surface of the water. After stirring, the film broke down into smaller sizes forming a strong hazy dispersion without reagglomeration or precipitation. No particles were observed on the glass surfaces.

While the invention has been illustrated with particular reference to bar soaps, it may be used for any compositions, liquid or solid, including aqueous hard surface cleaning solutions, as well as liquid and powder laundry detergents, which can form water-insoluble soap scum.

While the invention has been described with particular reference to certain embodiments thereof, it will be understood that changes and modifications may be made which are within the skill of the art. Accordingly, it is intended to be bound only by the following claims, in which:

What is claimed is:

1. A method of transforming water-insoluble soap scum into a stabilized, water-soluble dispersion which does not adhere to a hard surface which comprises applying a bar soap or powder laundry detergent composition containing about 0.05-5% by weight of an N-alkyl substituted lactam having the formula

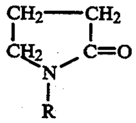

where R is a hydrophobic radical selected from linear and branched chain alkyl groups having from 5-27 carbon atoms to said soap scum while it is still present as a film.

2. A method according to claim 1 wherein R contains 5-18 carbon atoms.

3. A method according to claim 2 wherein said lactam is present in an amount of about 1-2% by weight.

4. A method according to claim 2 wherein said lactam contains 8 carbon atoms.

* * * * *